United States Patent
Sagata et al.

(10) Patent No.: US 10,047,316 B2
(45) Date of Patent: *Aug. 14, 2018

(54) FLUOROPOLYETHER COMPOUND, LUBRICANT, AND MAGNETIC DISK

(71) Applicant: MORESCO CORPORATION, Kobe-shi, Hyogo (JP)

(72) Inventors: Ryosuke Sagata, Kobe (JP); Haruo Kasai, Kobe (JP)

(73) Assignee: Moresco Corporation, Kobe-shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,511

(22) PCT Filed: Jun. 22, 2015

(86) PCT No.: PCT/JP2015/067918
§ 371 (c)(1),
(2) Date: Dec. 13, 2016

(87) PCT Pub. No.: WO2015/199037
PCT Pub. Date: Dec. 30, 2015

(65) Prior Publication Data
US 2017/0152456 A1   Jun. 1, 2017

(30) Foreign Application Priority Data
Jun. 24, 2014   (JP) ................. 2014-129681

(51) Int. Cl.
*F16C 33/20*   (2006.01)
*C10M 105/54*   (2006.01)
(Continued)

(52) U.S. Cl.
CPC ....... *C10M 105/54* (2013.01); *C08G 65/3318* (2013.01); *C10M 107/38* (2013.01); *G11B 5/725* (2013.01); *C10N 2240/204* (2013.01)

(58) Field of Classification Search
CPC ........ C10N 2240/204; C10M 2213/062; F16C 33/201
(Continued)

(56) References Cited

U.S. PATENT DOCUMENTS 6,608,009 B2   8/2003   Akada et al.
8,679,655 B2   3/2014   Kobayashi
(Continued)

FOREIGN PATENT DOCUMENTS

JP   2006-137904 A   6/2006
JP   2008-034064 A   2/2008
(Continued)

*Primary Examiner* — Vishal Vasisth
(74) *Attorney, Agent, or Firm* — Morgan, Lewis & Bockius LLP

(57) ABSTRACT

The disclosure provides a fluoropolyether compound represented by formula (1):

$$R^1-CH_2-R^2-CH_2-R^3$$

wherein $R^1$ is $C_1$-$C_{10}$ alkoxy; $R^2$ is $-(CF_2)_pO(CF_2O)_x(CF_2CF_2O)_y(CF_2CF_2CF_2O)_z(CF_2CF_2CF_2CF_2O)_w(CF_2)_p-$; x and y are each a real number of 0 to 30; z is a real number of 0 to 30; w is a real number of 0 to 20; p is an integer of 1 to 3; $R^3$ is $-OCH_2CH(OH)CH_2OH$, $-OCH_2CH(OH)CH_2OCH_2CH(OH)CH_2OH$, $-O(CH_2)_mOH$, or $-OCH_2(OH)CHCH_2-OC_6H_4-R^4$; m is an integer of 2 to 8; and $R^4$ is hydrogen, $C_1$-$C_4$ alkoxy, amino, or an amide residue; and also provides a lubricant having the compound and a magnetic disk.

18 Claims, 1 Drawing Sheet

(51) Int. Cl.
  *C10M 107/38*    (2006.01)
  *C08G 65/331*    (2006.01)
  *G11B 5/725*     (2006.01)

(58) Field of Classification Search
  USPC .......................................................... 508/106
  See application file for complete search history.

(56) References Cited

U.S. PATENT DOCUMENTS

| | | |
|---|---|---|
| 8,980,450 B2 | 3/2015 | Kobayashi |
| 2002/0183211 A1 | 12/2002 | Akada et al. |
| 2006/0106260 A1 | 5/2006 | Chiba et al. |
| 2010/0239887 A1 | 9/2010 | Kobayashi |
| 2010/0240560 A1 | 9/2010 | Shirakawa et al. |
| 2013/0209837 A1* | 8/2013 | Sagata ................... G11B 5/725 |
| | | 428/833 |
| 2014/0104724 A1 | 4/2014 | Shiroishi et al. |
| 2014/0147699 A1 | 5/2014 | Kobayashi |
| 2016/0137947 A1 | 5/2016 | Isobe et al. |

FOREIGN PATENT DOCUMENTS

| | | |
|---|---|---|
| JP | 4137447 B2 | 8/2008 |
| JP | 2009-270093 A | 11/2009 |
| JP | 2012-184275 A | 9/2012 |
| JP | 2014-081981 A | 5/2014 |
| WO | 2009/066784 A1 | 5/2009 |
| WO | 2009/078485 A1 | 6/2009 |
| WO | 2015/022871 A1 | 2/2015 |

\* cited by examiner

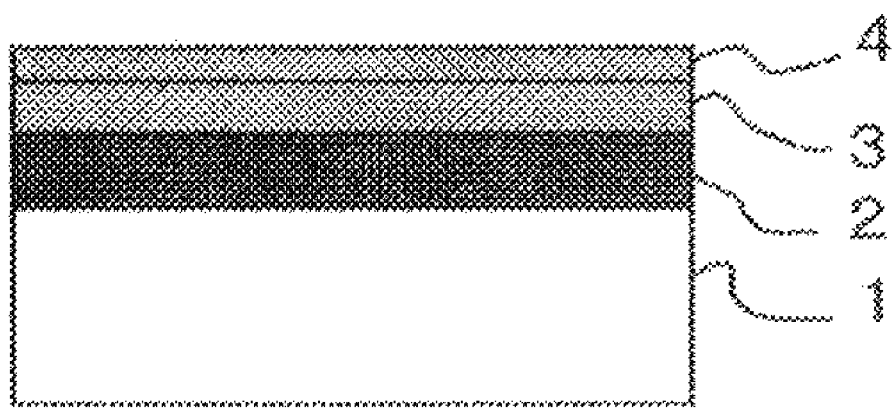

FLUOROPOLYETHER COMPOUND, LUBRICANT, AND MAGNETIC DISK

This application is a 371 of PCT/JP2015/067918, filed Jun. 22, 2015.

TECHNICAL FIELD

The present invention relates to a fluoropolyether compound, a lubricant, and a magnetic disk.

BACKGROUND ART

With the increased recording density of hard disk drives, the distance between a magnetic disk serving as a recording medium and a head for recording and reproducing information has become almost nil as they approach contact with each other. The magnetic disk surface is provided with a carbon protective film and a lubricant film (lubricant layer) to diminish abrasion caused by contact with the head or sliding of the head thereon, and to prevent contamination of the magnetic disk surface. The two layers protect the surface of the magnetic disk. In particular, the lubricant layer provided on the top must have various properties, such as long-term stability, chemical resistance, friction properties, and heat resistance.

Fluoropolyethers have often been used as lubricants for magnetic disks. However, fluoropolyether-based lubricants have low resistance to Lewis acid. Due to contact with the magnetic head, etc., the main chain is cut by alumina ($Al_2O_3$) contained in the magnetic head member, reducing the molecular weight of the lubricant. Subsequently, the transfer (pickup) of the lubricant with a reduced molecular weight to the magnetic head occurs, thereby reducing lubrication, and thus causing the hard disk drive to crash.

In order to address these problems, some techniques have been proposed in which a high electron-donating functional group is introduced into the fluoropolyether molecule, and the functional group comes into contact with an active alumina part in the magnetic head to induce an interaction, thereby inactivating alumina.

For example, PTL 1 proposes a fluoropolyether having a cyclophosphazene group at both terminals of the molecule. However, in a lubricant containing the compound disclosed in PTL 1, almost all highly electron-donating functional groups present in the lubricant molecule bind to the carbon protective film of a magnetic disk. Thus, the functional groups cannot come into contact with an active alumina part, and cannot inactivate active alumina.

PTL 2 discloses a fluoropolyether having two hydroxyl groups at both terminals of the molecule. The terminal hydroxyl groups of the compound disclosed in PTL 2 have decomposition resistance. However, almost all functional groups bind to the carbon protective film, as in PTL 1; therefore, alumina causes decomposition, as in PTL 1, and pickup occurs.

CITATION LIST

Patent Literature

PTL 1: JP4137447B
PTL 2: WO2009/066784

SUMMARY OF INVENTION

Technical Problem

An object of the present invention is to provide a compound that can inactivate active alumina in a magnetic head, a lubricant having decomposition resistance, and a magnetic disk using the lubricant.

Solution to Problem

The present inventors found that the above object can be achieved by using a fluoropolyether compound having an alkoxy group introduced into one terminal of the molecule. Thus, the present invention has been completed.

The present invention relates to the following compound, lubricants, and magnetic disk.

1. A fluoropolyether compound represented by formula (1):

$$R^1\text{—}CH_2\text{—}R^2\text{—}CH_2\text{—}R^3 \quad (1)$$

wherein $R^1$ is $C_1$-$C_{10}$ alkoxy;
$R^2$ is —$(CF_2)_pO(CF_2O)_x(CF_2CF_2O)_y(CF_2CF_2CF_2O)_z$ $(CF_2CF_2CF_2CF_2O)_w(CF_2)_p$—; x and y are each a real number of 0 to 30; z is a real number of 0 to 30; w is a real number of 0 to 20; p is an integer of 1 to 3;
$R^3$ is —$OCH_2CH(OH)CH_2OH$, —$OCH_2CH(OH)$ $CH_2OCH_2CH(OH)CH_2OH$, —$O(CH_2)_mOH$, or —$OCH_2$ $(OH)CHCH_2$—$OC_6H_4$—$R^4$; m is an integer of 2 to 8; and $R^4$ is hydrogen, $C_1$-$C_4$ alkoxy, amino, or an amide residue.

2. A lubricant comprising the fluoropolyether compound represented by formula (1) above.

3. The lubricant according to item 2, further comprising a lubricant for magnetic disks.

4. The lubricant according to item 3, wherein the lubricant according to item 2 and the lubricant for magnetic disks are contained at a weight ratio of 1:99 to 50:50.

5. A magnetic disk comprising, in this order, a substrate, and at least a recording layer and a protective layer, and having a lubricant layer on the surface of the protective layer, wherein the lubricant layer comprises the lubricant according to item 3 or 4.

Advantageous Effects of Invention

According to the fluoropolyether compound of the present invention having an alkoxy group and a hydroxyl group, the hydroxyl group at one terminal binds to a carbon protective film, and the alkoxy group at the other terminal is movable without binding to the carbon protective film, and comes into contact with the active alumina part of a magnetic head to thereby inactivate alumina.

Therefore, a lubricant comprising the fluoropolyether compound of the present invention has lubricity and decomposition resistance, and suppresses the transfer of the lubricant to a magnetic head, thereby preventing a crash of the hard disk drive.

BRIEF DESCRIPTION OF DRAWING

FIG. 1 is a cross-sectional diagram showing the configuration of a magnetic disk according to the present invention.

DESCRIPTION OF EMBODIMENTS

The compound of the present invention is represented by formula (1):

 (1)

wherein $R^1$ is $C_1$-$C_{10}$ alkoxy; $R^2$ is —$(CF_2)_pO(CF_2O)_x(CF_2CF_2O)_y(CF_2CF_2CF_2O)_z(CF_2CF_2CF_2CF_2O)_w(CF_2)_p$—; x and y are each a real number of 0 to 30; z is a real number of 0 to 30; w is a real number of 0 to 20; p is an integer of 1 to 3; $R^3$ is —$OCH_2CH(OH)CH_2OH$, —$OCH_2CH(OH)CH_2OCH_2CH(OH)CH_2OH$, —$O(CH_2)_mOH$, or —$OCH_2(OH)CHCH_2$—$OC_6H_4$—$R^4$; m is an integer of 2 to 8; and $R^4$ is hydrogen, $C_1$-$C_4$ alkoxy, amino, or an amide residue.

The number of carbon atoms in the alkyl moiety of the alkoxy (alkyloxy) group is 1 to 10, and preferably 1 to 5. This alkyl moiety acts as a Lewis base on the alumina part of a magnetic disk serving as a Lewis acid. Because the alkyl moiety of the alkoxy group has 1 to 10 carbon atoms, the alkyl moiety comes into contact with the alumina part of the magnetic head, while maintaining lubricity, without adhering to the carbon protective film of the magnetic disk, to develop an interaction, thereby suppressing the decomposition of the main chain of the lubricant.

The compound of the present invention represented by formula (1) is obtained by, for example, reacting (a) a linear fluoropolyether having a hydroxyl group at one terminal and a hydroxyl-containing alkoxy group at the other terminal with (A) a compound that reacts with a hydroxyl group to form an alkoxy group. Specifically, the compound of the present invention can be synthesized in the following manner.

[1] First, the fluoropolyether (a) is synthesized (step 1).

A linear fluoropolyether (b) having a hydroxyl group at both terminals is reacted with a compound (c) that reacts with a hydroxyl group to form a hydroxyl-containing alkoxy group. The reaction temperature is 20 to 90° C., and preferably 60 to 80° C. The reaction time is 5 to 20 hours, and preferably 10 to 15 hours. The amount of Compound (c) used is preferably 0.5 to 1.5 equivalents based on the amount of the fluoropolyether (b). Subsequently, for example, purification is performed by column chromatography, thereby giving a fluoropolyether (a). The reaction can be carried out in a solvent. Examples of solvents for use include t-butyl alcohol, dimethylformaldehyde, 1,4-dioxane, dimethylsulfoxide, dimethylacetamide, and the like. A reaction accelerator can be used in the reaction. Examples of the reaction accelerator include basic compounds, such as sodium, potassium t-butoxide, and sodium hydride.

The fluoropolyether (b) is represented by $HOCH_2$—$(CF_2)_p$ $O(CF_2O)_x(CF_2CF_2O)_y(CF_2CF_2CF_2O)_z(CF_2CF_2CF_2CF_2O)_w(CF_2)_p$—$CH_2OH$ (x and y are each a real number of 0 to 30, z is a real number of 0 to 30, w is a real number of 0 to 20, and p is an integer of 1 to 3). Specific examples of the fluoropolyether (b) include a compound represented by $HOCH_2CF_2CF_2CF_2O(CF_2CF_2CF_2CF_2O)_wCF_2CF_2CF_2CH_2OH$, a compound represented by $HOCH_2CF_2O(CF_2O)_x(CF_2CF_2O)_yCF_2CH_2OH$, a compound represented by $HOCH_2CF_2CF_2O(CF_2CF_2CF_2O)_zCF_2CF_2CH_2OH$, and the like. The number average molecular weight of these fluoropolyethers is generally 200 to 2000, preferably 400 to 1500, and more preferably 500 to 800. As used herein, the term "number average molecular weight" refers to a value obtained from $^{19}$F-NMR measured with JNM-ECX400 (JEOL Ltd.). In NMR measurement, the samples themselves were measured without being diluted with a solvent. The standard chemical shift that was used is a known peak, which is a portion of the backbone structure of a fluoropolyether. x and y are each preferably a real number of 0 to 15, and more preferably a real number of 0 to 10. It is preferable that x and y are each a real number of 0 to 10 because the molecular chain is more flat. z is preferably a real number of 1 to 15, and more preferably a real number of 1 to 10. It is preferable that z is a real number of 1 to 10 because the molecular chain is more flat. w is preferably a real number of 0 to 20. p is an integer of 1 to 3.

The fluoropolyether (b) has a molecular weight distribution. The molecular weight distribution (PD), which is represented by weight average molecular weight/number average molecular weight, of the fluoropolyether (b) is 1.0 to 1.5, preferably 1.0 to 1.3, and more preferably 1.0 to 1.1. The molecular weight distribution is a characteristic value obtained using HPLC-8220GPC (Tosoh Corporation), a column (PLgel Mixed E; Polymer Laboratories Ltd.), an HCFC-based alternative chlorofluorocarbon as an eluent, and a non-functional perfluoropolyether serving as a reference material.

Examples of Compound (c) include a compound having an epoxy group, a haloalkyl alcohol represented by $X(CH_2)_m$ OH, a phenoxy compound (c-1) having an epoxy group, and the like.

Examples of the compound having an epoxy group include glycidol, propylene oxide, glycidyl methyl ether, isobutylene oxide, and the like. Examples of haloalkyl alcohols include 2-chloroethanol, 3-chloropropanol, 4-chlorobutanol, 5-chloropentanol, 6-chlorohexanol, 7-chloroheptanol, 8-chlorooctanol, 2-bromoethanol, 3-bromopropanol, 4-bromobutanol, 5-bromopentanol, 6-bromohexanol, 7-bromoheptanol, 8-bromooctanol, 2-iodoethanol, 3-iodopropanol, 4-iodobutanol, 5-iodopentanol, 6-iodohexanol, 7-iodoheptanol, 8-iodooctanol, and the like.

In the haloalkyl alcohol represented by $X(CH_2)_mOH$, X is a halogen atom, such as chlorine, bromine, or iodine, and m is a real number of 2 to 8.

The phenoxy compound (c-1) having an epoxy group is represented by the following formula:

 (c-1)

$R^4$ is hydrogen, $C_1$-$C_4$ alkoxy, amino, an amide residue, or the like.

Examples of $C_1$-$C_4$ alkoxy include methoxy, ethoxy, propoxy, butoxy, and the like. Examples of amino groups include amino, methylamino, dimethylamino, ethylamino, diethylamino, and the like. Examples of amide residues include acetamide (—$NHCOCH_3$), propionamide (—$NHCOC_2H_5$), and the like.

Specific examples of Compound (c-1) include glycidyl 4-methoxyphenyl ether, glycidyl 4-ethoxyphenyl ether, glycidyl 4-propoxyphenyl ether, glycidyl 4-butoxyphenyl ether, glycidyl 4-aminophenyl ether, glycidyl 4-methylaminophenyl ether, glycidyl 4-dimethylaminophenyl ether, glycidyl 4-ethylaminophenyl ether, glycidyl 4-diethylaminophenyl ether, glycidyl 4-acetamidophenyl ether, glycidyl 4-propionamidophenyl ether, and the like.

For example, when $HOCH_2CF_2O(CF_2CF_2O)_y(CF_2O)_x$ $CF_2CH_2OH$ is used as the fluoropolyether (b), and glycidol is used as Compound (c), the reaction thereof produces $HOCH_2CH(OH)CH_2OCH_2CF_2O(CF_2CF_2O)_y(CF_2O)_x$ $CF_2CH_2OH$, $HOCH_2CH(OH)CH_2OCH_2CH(OH)$ $CH_2OCH_2CF_2O(CF_2CF_2O)_y(CF_2O)_xCF_2CH_2OH$, or the like as the fluoropolyether (a).

When $HOCH_2CF_2O(CF_2CF_2O)_y(CF_2O)_xCF_2CH_2OH$ is used as the fluoropolyether (b), and 2-bromoethanol is used as Compound (c), $HOCH_2CH_2OCH_2CF_2O(CF_2CF_2O)_y$ $(CF_2O)_xCF_2CH_2OH$ is produced as the fluoropolyether (a).

Moreover, when $HOCH_2CF_2O(CF_2CF_2O)_y(CF_2O)_x$ $CF_2CH_2OH$ is used as the fluoropolyether (b), and glycidyl 4-methoxyphenyl ether is used as Compound (c), $CH_3O-C_6H_4O-CH_2CH(OH)CH_2OCH_2CF_2O(CF_2CF_2O)_y$, $(CF_2O)_x\ CF_2CH_2OH$ is produced as the fluoropolyether (a).

[2] Next, the compound of the present invention is synthesized from the fluoropolyether (a) obtained in step 1 (step 2).

The fluoropolyether (a) obtained in step 1 is reacted with Compound (A) in the presence of a base. The reaction temperature is 20 to 90° C., and preferably 60 to 80° C. The reaction time is 5 to 20 hours, and preferably 10 to 15 hours. It is preferable that 1.0 to 2.0 equivalents of Compound (A) and 0.05 to 0.1 equivalents of catalyst are used based on the amount of the fluoropolyether (a). Examples of catalysts for use include alkali compounds, such as sodium t-butoxide and potassium t-butoxide. The reaction can be carried out in a solvent. Examples of solvents for use include t-butanol, toluene, and xylene. Thereafter, the reaction mixture is, for example, washed with water and dehydrated. Compound (1) of the present invention can thereby be obtained.

Alkyl halide can be used as Compound (A). Examples of halogen include chlorine, bromine, iodine, and the like. The number of carbon atoms of the alkyl is generally 1 to 10, and preferably 1 to 5. Moreover, the alkyl is preferably linear alkyl. Examples of alkyl halide include 1-bromopropane, 1-chloropropane, 1-iodopropane, 1-bromobutane, 1-chlorobutane, 1-iodobutane, 1-bromopentane, 1-chloropentane, 1-iodopentane, 1-bromohexane, 1-chlorohexane, 1-iodohexane, 1-bromoheptane, 1-chloroheptane, 1-iodoheptane, 1-bromooctane, 1-chlorooctane, 1-iodooctane, 1-bromononane, 1-chlorononane, 1-iodononane, 1-bromodecane, 1-chlorodecane, 1-iododecane, and the like.

The compound of the present invention adheres to the carbon protective film only at one terminal, and an alkoxy group is present on the surface side of the lubricant film; therefore, while ensuring lubricity, the alkoxy group at one terminal can come into contact with the alumina part of a magnetic head to thereby inactivate active alumina. Therefore, the compound of the present invention functions as a lubricant having decomposition resistance.

The lubricant comprising the compound of the present invention is preferably used as mixed with another fluoropolyether-based lubricant generally used as a lubricant for magnetic disks, such as Fomblin Zdol, Ztetraol, Zdol TX, AM (all manufactured by Solvay Solexis), Denmum (Daikin Industries, Ltd.), and Krytox (DuPont). These lubricants for magnetic disks may be used singly or in a combination of two or more. The mixing ratio of the lubricant comprising the compound of the present invention and the lubricant for magnetic disks is preferably 1:99 to 50:50, and more preferably 5:95 to 20:80, by weight ratio.

According to the lubricant containing a lubricant comprising the compound of the present invention and a lubricant for magnetic disks, the hydroxyl group at one terminal of the lubricant comprising the compound of the present invention and the lubricant for magnetic disks interact with a carbon protective film to thereby ensure lubricity, and the alkoxy group at the other terminal of the lubricant comprising the compound of the present invention can come into contact with an alumina part in a magnetic head to thereby inactivate active alumina and reduce the pickup.

When applying the lubricant of the present invention onto the surface of a magnetic disk, it is preferable to dilute the lubricant with a solvent before applying the lubricant. Examples of solvents include PF-5060, PF-5080, HFE-7100, and HFE-7200 (all manufactured by 3M); and Vertrel-XF (DuPont). The diluted lubricant has a concentration of 1 wt % or less, and preferably 0.001 to 0.1 wt %.

The compound of the present invention can be used as a lubricant for reducing the spacing between a magnetic disk and a head inside a magnetic disk apparatus, and improving the durability against sliding. Accordingly, the compound is usable not only for magnetic disks, but also for magnetic heads, photomagnetic recording devices, and magnetic tapes, which all have a carbon protective film; a surface protective film for organic materials, such as plastics; and a surface protective film for inorganic materials, such as $Si_3N_4$, SiC, and $SiO_2$.

FIG. 1 is a cross-sectional diagram showing a magnetic disk according to the present invention. The magnetic disk of the present invention comprises at least one recording layer 2 formed on a substrate 1, a protective layer 3 formed on the at least one recording layer 2, and a lubricant layer 4 comprising the compound of the present invention and a lubricant for magnetic disks formed on the protective layer 3 as the outermost layer. Examples of substrates include aluminium alloys, ceramics such as glass, and polycarbonate.

Examples of constituent materials for a magnetic layer, which is the recording layer of the magnetic disk, include primarily elements capable of forming a ferromagnet, such as iron, cobalt, and nickel; alloys containing chromium, platinum, tantalum, or the like in addition to such elements; and oxides thereof. The layer of these materials is formed by a technique, such as plating or sputtering. Examples of materials for the protective layer include carbon, SiC, $SiO_2$, and the like. The layer of these materials is formed by sputtering or CVD.

Lubricant layers presently available have a thickness of 30 Å or less. Thus, when a lubricant having a viscosity of about 100 mPa·s or more at 20° C. is applied as it is, the resulting film could have an excessively large thickness. Therefore, a lubricant dissolved in a solvent is used in coating. If the lubricant of the present invention, which is also used as a mixture of the compound of the present invention and another lubricant, is dissolved in a solvent, it is easier to desirably control the film thickness. However, the concentration varies depending on the coating technique and conditions, the mixing ratio, and the like. The film thickness formed by the lubricant of the present invention is preferably 5 to 15 Å.

To facilitate the adsorption of the lubricant to the underlayer, a heat treatment and/or an ultraviolet treatment can be carried out. The heat treatment is typically carried out at a temperature of 60 to 150° C., and preferably 80 to 150° C. The ultraviolet treatment is preferably carried out using ultraviolet rays having dominant wavelengths of 185 nm and 254 nm.

The magnetic disk of the present invention can be used in a magnetic disk apparatus comprising: a magnetic disk drive that accommodates the disk and comprises a magnetic head for recording, reproducing and erasing information, and a motor for rotating the disk; and a control system for controlling the magnetic disk drive.

The magnetic disk according to the present invention and a magnetic disk apparatus comprising the magnetic disk can be used, for example, in external memories for electronic computers and word processors. The disk and apparatus can also be used in various devices, such as navigation systems, games, cellular phones, and PHS; internal or external recording devices for building security, power plant administration systems, and power plant control systems; and the like.

EXAMPLES

The following Examples, etc., will describe the present invention in detail. However, the present invention is not limited to the Examples, etc. Note that $^{19}$F-NMR was measured without a solvent and using as the standard chemical shift a known peak that is a portion of the backbone structure of a fluoropolyether, and $^1$H-NMR was measured without a solvent and using D$_2$O as the standard substance.

Example 1

Synthesis of CH$_3$CH$_2$CH$_2$OCH$_2$CF$_2$O(CF$_2$O)$_x$(CF$_2$CF$_2$O)$_y$CF$_2$CH$_2$OCH$_2$CH(OH)CH$_2$OH (Compound 1)

In an argon atmosphere, a mixture of t-butyl alcohol (40 g), 100 g of a fluoropolyether represented by HO—CH$_2$CF$_2$O(CF$_2$O)$_x$(CF$_2$CF$_2$O)$_y$CF$_2$CH$_2$—OH (number average molecular weight: 1720, molecular weight distribution: 1.20), potassium t-butoxide (0.7 g), and glycidol (5 g) was stirred at 70° C. for 14 hours. Subsequently, the mixture was washed with water, dehydrated, and purified by silica gel column chromatography, thereby giving 95 g of perfluoropolyether (average molecular weight: 1842) having one hydroxyl group at one terminal and two hydroxyl groups at the other terminal. This compound (95 g) was dissolved in t-butyl alcohol (43 g), and potassium t-butoxide (6 g) and 1-bromopropane (15 g) were added thereto, followed by stirring at 70° C. for 14 hours. The mixture was then washed with water and dehydrated, followed by purification by distillation, thereby giving 65 g of Compound 1.

Compound 1 was a colorless transparent liquid, and had a density of 1.74 g/cm$^3$ at 20° C. Compound 1 was identified by NMR as shown below.

$^{19}$F-NMR (solvent: none, standard substance: OCF$_2$C$\underline{F}_2$CF$_2$C$\underline{F}_2$O in the obtained product, which was taken as −125.8 ppm)

δ=−52.1 ppm, −53.7 ppm, −55.4 ppm
[16F, CH$_3$CH$_2$CH$_2$OCH$_2$CF$_2$O(C$\underline{F}_2$O)$_x$(CF$_2$CF$_2$O)$_y$CF$_2$CH$_2$OCH$_2$CH(OH)CH$_2$OH],
δ=−89.1 ppm, −90.7 ppm
[32F, CH$_3$CH$_2$CH$_2$OCH$_2$CF$_2$O(CF$_2$O)$_x$(C$\underline{F}_2$C$\underline{F}_2$O)$_y$CF$_2$CH$_2$OCH$_2$CH(OH)CH$_2$OH],
δ=−78.6 ppm, −80.6 ppm
[2F, CH$_3$CH$_2$CH$_2$OCH$_2$CF$_2$O(CF$_2$O)$_x$(CF$_2$CF$_2$O)$_y$C$\underline{F}_2$CH$_2$OCH$_2$CH(OH)CH$_2$OH],
δ=−78.0 ppm, −80.1 ppm
[2F, CH$_3$CH$_2$CH$_2$OCH$_2$C$\underline{F}_2$O(CF$_2$O)$_x$(CF$_2$CF$_2$O)$_y$CF$_2$CH$_2$OCH$_2$CH(OH)CH$_2$OH],
x=8.9, y=8.7
$^1$H-NMR (solvent: none, standard substance: D$_2$O)
δ=3.2-3.8 ppm
[11H, CH$_3$CH$_2$C$\underline{H}_2$OC$\underline{H}_2$—CF$_2$O(CF$_2$O)$_x$(CF$_2$CF$_2$O)$_y$CF$_2$C$\underline{H}_2$—O—C$\underline{H}_2$C$\underline{H}$(OH)C$\underline{H}_2$OH]
δ=0.5-1.2 ppm
[7H, C$\underline{H}_3$C$\underline{H}_2$C$\underline{H}_2$OCH$_2$—CF$_2$O(CF$_2$O)$_x$(CF$_2$CF$_2$O)$_y$CF$_2$C$\underline{H}_2$—O—CH$_2$CH(OH)CH$_2$OH]

Example 2

Synthesis of CH$_3$CH$_2$CH$_2$OCH$_2$CF$_2$CF$_2$O(CF$_2$CF$_2$CF$_2$O)$_z$CF$_2$CF$_2$CH$_2$OCH$_2$CH(OH)CH$_2$OH (Compound 2)

Compound 2 (60 g) was obtained in the same manner as in Example 1, except that a fluoropolyether represented by HO—CH$_2$CF$_2$CF$_2$O(CF$_2$CF$_2$CF$_2$O)$_z$CF$_2$CF$_2$—CH$_2$—OH was used in place of the fluoropolyether represented by HO—CH$_2$CF$_2$O(CF$_2$O)$_x$(CF$_2$CF$_2$O)$_y$CF$_2$—CH$_2$—OH used in Example 1.

Compound 2 was a colorless transparent liquid, and had a density of 1.80 g/cm$^3$ at 20° C. Compound 2 was identified by NMR as shown below.

$^{19}$F-NMR (solvent: none, standard substance: OCF$_2$C$\underline{F}_2$CF$_2$O in the obtained product, which was taken as −129.7 ppm)

δ=−129.7 ppm
[18F, —OCF$_2$C$\underline{F}_2$CF$_2$O—],
δ=−83.7
[36F, —OC$\underline{F}_2$CF$_2$C$\underline{F}_2$O—],
δ=−124.2 ppm
[2F, CH$_3$CH$_2$CH$_2$OCH$_2$CF$_2$CF$_2$O(CF$_2$CF$_2$CF$_2$O)$_z$C$\underline{F}_2$CF$_2$CH$_2$OCH$_2$CH(OH)CH$_2$OH],
δ=−122.4 ppm
[2F, CH$_3$CH$_2$CH$_2$OCH$_2$CF$_2$C$\underline{F}_2$O(CF$_2$CF$_2$CF$_2$O)$_z$CF$_2$CF$_2$CH$_2$OCH$_2$CH(OH)CH$_2$OH],
δ=−86.5 ppm
[4F, CH$_3$CH$_2$CH$_2$OCH$_2$C$\underline{F}_2$CF$_2$O(CF$_2$CF$_2$CF$_2$O)$_z$CF$_2$C$\underline{F}_2$CH$_2$OCH$_2$CH(OH)CH$_2$OH]
z=9.3
$^1$H-NMR (solvent: none, standard substance: D$_2$O)
δ=3.2-3.8 ppm
[11H, CH$_3$CH$_2$C$\underline{H}_2$OC$\underline{H}_2$—CF$_2$CF$_2$O(CF$_2$CF$_2$CF$_2$O)$_z$CF$_2$CF$_2$C$\underline{H}_2$—O—C$\underline{H}_2$CH(OH)C$\underline{H}_2$OH]
δ=0.5-1.2 ppm
[7H, C$\underline{H}_3$C$\underline{H}_2$C$\underline{H}_2$OCH$_2$—CF$_2$CF$_2$O(CF$_2$CF$_2$CF$_2$O)$_z$CF$_2$CF$_2$C$\underline{H}_2$—O—CH$_2$CH(OH)CH$_2$OH]

Example 3

Synthesis of CH$_3$CH$_2$CH$_2$OCH$_2$CF$_2$CF$_2$CF$_2$O(CF$_2$CF$_2$CF$_2$CF$_2$O)$_w$CF$_2$CF$_2$CF$_2$CH$_2$OCH$_2$CH(OH)CH$_2$OH (Compound 3)

Compound 3 (59 g) was obtained in the same manner as in Example 1, except that a fluoropolyether represented by HO—CH$_2$CF$_2$CF$_2$CF$_2$O(CF$_2$CF$_2$CF$_2$CF$_2$O)$_w$CF$_2$CF$_2$CF$_2$—CH$_2$—OH was used in place of the fluoropolyether represented by HO—CH$_2$CF$_2$O(CF$_2$O)$_x$(CF$_2$CF$_2$O)$_y$CF$_2$—CH$_2$—OH used in Example 1.

Compound 3 was a colorless transparent liquid, and had a density of 1.72 g/cm$^3$ at 20° C. Compound 3 was identified by NMR as shown below.

$^{19}$F-NMR (solvent: none, standard substance: $OCF_2CF_2CF_2CF_2O$ in the obtained product, which was taken as $-125.8$ ppm)

δ=−83.7 ppm

[24F, $CH_3CH_2CH_2OCH_2CF_2CF_2CF_2O(CF_2CF_2CF_2CF_2O)_wCF_2CF_2CF_2CH_2OCH_2CH(OH)CH_2OH$],

δ=−123.3 ppm

[2F, $CH_3CH_2CH_2OCH_2CF_2CF_2CF_2O(CF_2CF_2CF_2CF_2O)_wCF_2CF_2CF_2CH_2OCH_2CH(OH)CH_2OH$],

δ=−121.5 ppm

[2F, $CH_3CH_2CH_2OCH_2CF_2CF_2CF_2O(CF_2CF_2CF_2CF_2O)_wCF_2CF_2CF_2CH_2OCH_2CH(OH)CH_2OH$],

δ=−125.8 ppm

[12F, $-OCF_2CF_2CF_2CF_2O-$],

δ=−127.6 ppm

[4F, $CH_3CH_2CH_2OCH_2CF_2CF_2CF_2O(CF_2CF_2CF_2CF_2O)_wCF_2CF_2CF_2CH_2OCH_2CH(OH)CH_2OH$]

w=5.2

$^1$H-NMR (solvent: none, standard substance: $D_2O$)

δ=3.2-3.8 ppm

[11H, $CH_3CH_2CH_2OCH_2CF_2CF_2CF_2O(CF_2CF_2CF_2CF_2O)_wCF_2CF_2CF_2CH_2OCH_2CH(OH)CH_2OH$]

δ=0.5-1.2 ppm

[7H, $CH_3CH_2CH_2OCH_2CF_2CF_2CF_2O(CF_2CF_2CF_2CF_2O)_wCF_2CF_2CF_2CH_2OCH_2CH(OH)CH_2OH$]

Comparative Example 1

A compound of formula (5) ($HOCH_2CH(OH)CH_2OCH_2CF_2CF_2CF_2O(CF_2CF_2CF_2CF_2O)_zCF_2CF_2CH_2OCH_2CH(OH)CH_2OH$) disclosed in paragraph [0004] of PTL 2 (WO2009/066784) mentioned above was used as Compound 4. Compound 4 was produced by the following production method, and had two hydroxyl groups at both terminals of the molecule.

In an argon atmosphere, a mixture of t-butyl alcohol (41 g), 95 g of a fluoropolyether represented by $HO-CH_2CF_2CF_2CF_2O(CF_2CF_2CF_2CF_2O)_zCF_2CF_2CH_2-OH$ (number average molecular weight: 1850, molecular weight distribution: 1.25), potassium t-butoxide (0.8 g), and glycidol (11 g) was stirred at 70° C. for 14 hours. Subsequently, the mixture was washed with water, dehydrated, and purified by silica gel column chromatography, thereby giving 90 g of Compound 4 (average molecular weight: 1936) having two hydroxyl groups at both terminals.

Compound 4 was a colorless transparent liquid, and had a density of 1.75 g/cm$^3$ at 20° C. Compound 4 was identified by NMR, as shown below.

$^{19}$F-NMR (solvent: none, standard substance: $OCF_2CF_2CF_2O$ in the obtained product, which was taken as $-129.7$ ppm)

δ=−129.7 ppm

[26F, $-OCF_2CF_2CF_2O-$],

δ=−83.7

[52F, $-OCF_2CF_2CF_2O-$],

δ=−124.2 ppm

[4F, $-OCF_2CF_2CH_2OCH_2CH(OH)CH_2OH$],

δ=−86.5 ppm

[4F, $-OCF_2CF_2CH_2OCH_2CH(OH)CH_2OH$]

z=13.0

$^1$H-NMR (solvent: none, standard substance: $D_2O$)

δ=3.2-3.8 ppm

[18H, $HO-CH_2CH(OH)CH_2O-CH_2CF_2CF_2O(CF_2CF_2CF_2O)_zCF_2CF_2CH_2-O-CH_2CH(OH)CH_2OH$]

Test Example 1: Evaluation of Decomposition Resistance to Aluminium Oxide 20 wt % of $Al_2O_3$ was added to each lubricant (Compounds 1 to 4), and the mixtures were strongly shaken, followed by further mixing by ultrasound, thereby preparing samples for evaluation of decomposition resistance. Evaluation of the decomposition resistance was conducted by measuring the weight decrease of the lubricants heated at 250° C. for 100 minutes using a thermal analyzer (TG/TDA). The measurement was conducted in a nitrogen atmosphere using 20 mg of each sample. Table 1 shows the results.

TABLE 1

| | Decrease in Weight (%) |
|---|---|
| Compound 1 | <1 |
| Compound 2 | <1 |
| Compound 3 | <1 |
| Compound 4 | <10 |

Test Example 2: Measurement of Bonded Ratio

Compound 1 synthesized in Example 1 was dissolved in Vertrel-XF, produced by DuPont. A magnetic disk having a diameter of 2.5 inches was dipped in the resulting solution for 1 minute, and lifted out at 2 mm/s. The lubricant-applied disk was placed for 10 to 20 seconds in an ultraviolet irradiation device equipped with a low-pressure mercury lamp emitting ultraviolet light having wavelengths of 185 nm and 254 nm. Here, in order to prevent formation of ozone, the atmosphere inside the ultraviolet irradiation device was replaced with nitrogen in advance. Then, the average film thickness of the compound on the disk was measured by a Fourier Transform Infrared Spectrometer (FT-IR). The thickness measured was defined as fÅ. Subsequently, the disk was immersed in Vertrel-XF for 10 minutes, lifted out at 10 mm/s, and then allowed to stand at room temperature to vaporize the solvent. Then, the average film thickness of the compound remaining on the disk was measured by ET-IR. The thickness measured was defined as bÅ. The strength of adhesion of the compound to the disk was evaluated based on the generally used bonded ratio. The bonded ratio is represented by the following formula:

Bonded ratio (%)=100×b/f

TABLE 2

| | Bonded Ratio (%) |
|---|---|
| Compound 1 | 60 |
| Compound 2 | 62 |
| Compound 3 | 65 |
| Compound 4 | 88 |

These results confirmed that Compound 4 formed a bond with the surface of the magnetic disk at both terminals of the molecule, while Compounds 1 to 3 of the present invention formed a bond with the disk surface only at one terminal having a polar group.

Test Example 3: Evaluation of Pickup

Compound 4 and a mixture of Compound 1 and Compound 4 (15 wt %: 85 wt %) were each dissolved in Vertrel-XF, produced by DuPont. The concentration of the lubricant in each solution was 0.05 wt %. Magnetic disks having a diameter of 2.5 inches were individually dipped in each solution for 1 minute, and lifted out at 2 mm/s. Subsequently, a magnetic head was mounted, and the prepared magnetic disks were each rotated at a high speed of 5400 rpm. Thereafter, the amount of the lubricant adhering to the magnetic head was measured.

TABLE 3

|  | Compound 4 | Mixture of Compounds 1 and 4 |
| --- | --- | --- |
| Pickup amount (au) Film thickness 10 Å | 15 | 10 |
| Pickup amount (au) Film thickness 13 Å | 33 | 5 |

These results confirmed that the lubricant comprising a fluoropolyether-based lubricant and the compound of the present invention having an alkoxy group at one terminal and a hydroxyl group at the other terminal could reduce the pickup.

REFERENCE SIGNS LIST

1. Substrate
2. Recording Layer
3. Protective Layer
4. Lubricant Layer

The invention claimed is:

1. A fluoropolyether compound represented by formula (1):

wherein $R^1$ is $C_1$-$C_5$ alkoxy;
$R^2$ is $—(CF_2)_pO(CF_2O)_x(CF_2CF_2O)_y(CF_2CF_2CF_2O)_z(CF_2CF_2CF_2CF_2O)_w(CF_2)_p—$; x and y are each a real number of 0 to 30; z is a real number of 0 to 30; w is a real number of 0 to 20; p is an integer of 1 to 3; and
$R^3$ is $—OCH_2CH(OH)CH_2OH$, $—OCH_2CH(OH)CH_2OCH_2CH(OH)CH_2OH$, or $—O(CH_2)_mOH$; m is an integer of 2 to 8.

2. A lubricant comprising a fluoropolyether compound represented by formula (1):

wherein $R^1$ is $C_1$-$C_5$ alkoxy;
$R^2$ is $—(CF_2)_pO(CF_2O)_x(CF_2CF_2O)_y(CF_2CF_2CF_2O)_z(CF_2CF_2CF_2CF_2O)_w(CF_2)_p—$; x and y are each a real number of 0 to 30; z is a real number of 0 to 30; w is a real number of 0 to 20; p is an integer of 1 to 3; and
$R^3$ is $—OCH_2CH(OH)CH_2OH$, $—OCH_2CH(OH)CH_2OCH_2CH(OH)CH_2OH$, or $—O(CH_2)_mOH$; m is an integer of 2 to 8.

3. The lubricant according to claim 2, further comprising a lubricant for magnetic disks.

4. The lubricant according to claim 3, wherein the lubricant according to claim 2 and the lubricant for magnetic disks are contained at a weight ratio of 1:99 to 50:50.

5. A magnetic disk comprising, in this order, a substrate, and at least a recording layer and a protective layer, and having a lubricant layer on the surface of the protective layer, wherein the lubricant layer comprises the lubricant according to claim 3.

6. A magnetic disk comprising, in this order, a substrate, and at least a recording layer and a protective layer, and having a lubricant layer on the surface of the protective layer, wherein the lubricant layer comprises the lubricant according to claim 4.

7. The fluoropolyether compound according to claim 1, wherein $R^3$ is $—OCH_2CH(OH)CH_2OH$.

8. The fluoropolyether compound according to claim 1, wherein $R^3$ is $—OCH_2CH(OH)CH_2OCH_2CH(OH)CH_2OH$.

9. The fluoropolyether compound according to claim 1, wherein $R^3$ is $—O(CH_2)_mOH$.

10. The lubricant according to claim 2, wherein $R^3$ is $—OCH_2CH(OH)CH_2OH$.

11. The lubricant according to claim 2, wherein $R^3$ is $—OCH_2CH(OH)CH_2OCH_2CH(OH)CH_2OH$.

12. The lubricant according to claim 2, wherein $R^3$ is $—O(CH_2)_mOH$.

13. The fluoropolyether compound according to claim 1, wherein x is not 0.

14. The fluoropolyether compound according to claim 1, wherein y is not 0.

15. The fluoropolyether compound according to claim 1, wherein z is not 0.

16. The fluoropolyether compound according to claim 1, wherein w is not 0.

17. The fluoropolyether compound according to claim 1, wherein x and y are each a real number of 0 to 10.

18. The fluoropolyether compound according to claim 1, wherein z is a real number of 0 to 10.

* * * * *